(12) United States Patent
Chen et al.

(10) Patent No.: US 11,318,048 B2
(45) Date of Patent: May 3, 2022

(54) METHODS AND SYSTEMS FOR LARGE SPOT RETINAL LASER TREATMENT

(71) Applicant: IRIDEX Corporation, Mountain View, CA (US)

(72) Inventors: Howard Chen, San Jose, CA (US); George Marcellino, Santa Cruz, CA (US)

(73) Assignee: IRIDEX Corporation, Mountain View, CA (US)

( * ) Notice: Subject to any disclaimer, the term of this patent is extended or adjusted under 35 U.S.C. 154(b) by 230 days.

(21) Appl. No.: 16/556,827

(22) Filed: Aug. 30, 2019

(65) Prior Publication Data

US 2020/0069463 A1    Mar. 5, 2020

Related U.S. Application Data

(60) Provisional application No. 62/725,571, filed on Aug. 31, 2018.

(51) Int. Cl.
*A61F 9/008* (2006.01)
*A61B 5/398* (2021.01)

(52) U.S. Cl.
CPC .............. *A61F 9/008* (2013.01); *A61B 5/398* (2021.01); *A61F 2009/00851* (2013.01); *A61F 2009/00863* (2013.01); *A61F 2009/00891* (2013.01)

(58) Field of Classification Search
CPC ............................................ A61F 2009/00863
USPC ....................................................... 606/4–6
See application file for complete search history.

(56) References Cited

U.S. PATENT DOCUMENTS

| 4,874,237 | A | 10/1989 | Cringle |
| 5,154,174 | A | 10/1992 | Hawlina |
| 6,743,221 | B1 | 6/2004 | Hobart et al. |
| 7,150,530 | B2 | 12/2006 | Artsyukhovich et al. |
| 7,232,240 | B2 | 6/2007 | Kosnik et al. |
| 7,474,680 | B2 | 1/2009 | Gruhlke et al. |
| 7,771,417 | B2 * | 8/2010 | Telfair .................... H01S 3/109 606/5 |
| 9,026,189 | B2 | 5/2015 | Garcia et al. |
| 9,381,116 | B2 | 7/2016 | Luttrull et al. |

(Continued)

OTHER PUBLICATIONS

Pitkanen et al., "A Novel Method for Mouse Retinal Temperature Determination Based on ERG Photoresponses", Annals of Biomedical Engineering, vol. 45, No. 10, Oct. 2017, pp. 2360-2372.

(Continued)

*Primary Examiner* — John R Downey
(74) *Attorney, Agent, or Firm* — Kilpatrick Townsend & Stockton LLP

(57) ABSTRACT

In some embodiments, a system for providing a therapeutic treatment to a patient's eye includes a treatment beam source configured to transmit a treatment beam along a treatment beam path. The system further includes a processor coupled to the treatment beam source, the processor being configured to direct the treatment beam onto retinal tissue of the patient's eye and deliver a series of short duration pulses from the treatment beam onto the retinal tissue at a first treatment spot to treat the retinal tissue. In some embodiments, a pre-treatment evaluation method using electroretinography (ERG) data may be used to predict effects of treatment beams at different power values and to determine optimal power values.

27 Claims, 9 Drawing Sheets

(56) References Cited

U.S. PATENT DOCUMENTS

| | | | |
|---|---|---|---|
| 9,402,366 B2 | 8/2016 | Holliday et al. | |
| 9,707,129 B2 | 7/2017 | Yee | |
| 9,949,638 B2 | 4/2018 | Creasey et al. | |
| 2004/0233388 A1* | 11/2004 | Artsyukhovich | A61F 9/00821 351/216 |
| 2005/0070896 A1 | 3/2005 | Daniel et al. | |
| 2006/0187978 A1* | 8/2006 | Telfair | H01S 3/109 372/25 |
| 2013/0085481 A1* | 4/2013 | Dick | A61F 9/007 606/4 |
| 2013/0110206 A1* | 5/2013 | Yee | A61F 9/00823 607/89 |
| 2013/0116670 A1* | 5/2013 | Artsyukhovich | A61B 3/1233 606/4 |
| 2013/0317487 A1* | 11/2013 | Luttrull | A61B 18/20 606/5 |
| 2014/0005756 A1 | 1/2014 | Liu et al. | |
| 2014/0328461 A1 | 11/2014 | Gertner et al. | |
| 2016/0067086 A1* | 3/2016 | Tedford | A61N 5/0622 606/4 |
| 2016/0346126 A1* | 12/2016 | Luttrull | A61F 9/00823 |
| 2018/0008460 A1* | 1/2018 | Tanzer | A61B 3/12 |
| 2018/0125708 A1* | 5/2018 | Bohme | A61F 9/00821 |
| 2018/0339170 A1* | 11/2018 | Luttrull | A61N 5/025 |

OTHER PUBLICATIONS

Quintana et al., "Electroretinography: A biopotential to assess the function / dysfunction of the retina.", Journal of Physics: Conference Series 705, 2016, pp. 1-10.

* cited by examiner

702 — Delivering, via a treatment beam from a treatment beam source, a therapeutic treatment to retinal tissue of the patient's eye. The delivered therapeutic treatment includes a treatment spot on the retinal tissue at an intensity below that which effects coagulative damage so as to minimize damage to the retinal tissue. The treatment beam is delivered at an infrared wavelength, a power from 1 to 100 W, and along a treatment beam path and the treatment spot ranges from 1 to 6 mm in diameter.

802 — Delivering an aiming beam from an aiming beam source along an aiming beam path, the aiming beam passing through a concave lens disposed between the patient and the aiming beam and configured to diverge the aiming beam around a treatment beam source such that only a portion of the aiming beam is blocked by the treatment beam source prior to passing through a convex lens disposed between the patient and the treatment beam source.

800

804 — Defining, via the aiming beam, a visible treatment boundary on retinal tissue of the patient, the aiming beam passing through the convex lens to be focused onto the retinal tissue to define the treatment boundary.

806 — Delivering, via a treatment beam from the treatment beam source, a therapeutic treatment to retinal tissue of the patient's eye at a treatment spot on the retinal tissue disposed within the treatment boundary, the treatment beam being delivered along a treatment beam path extending non-coaxial relative to the aiming beam path.

FIG. 8

METHODS AND SYSTEMS FOR LARGE SPOT RETINAL LASER TREATMENT

CROSS REFERENCE TO RELATED APPLICATION DATA

The present application claims the benefit under 35 USC § 119(e) of U.S. Provisional Appln. No. 62/725,571 filed Aug. 31, 2018; the full disclosure of which is incorporated herein by reference in its entirety for all purposes.

BACKGROUND

Therapeutic lasers are often used to treat various conditions of the eye. For example, a specific type of condition that may be treated with such lasers is diabetic retinopathy. Diabetic retinopathy, is damage to the retina that is due to complications of diabetes. If left untreated, diabetic retinopathy can eventually lead to blindness. Diabetic retinopathy typically results from microvascular retinal changes. For example, diabetic induced effects may damage tissue of the eye, which may change the formation of the blood-retinal barrier and make the retinal blood vessels become more permeable. In treating such conditions, one or more light beams may be directed into the eye and/or onto retinal tissue to cause photocoagulation of the tissue so as to finely cauterize ocular blood vessels and/or prevent blood vessel growth to induce various therapeutic benefits. Laser photocoagulation is commonly used for early stages of retinopathy.

In providing laser photocoagulation treatments, however, it is important to avoid damaging sensitive tissue of the eye, such as the fovea, macula, and the like. In certain instances, it may be desired to treat tissue close to or at one or more of these areas while ensuring that damage to such areas is avoided. Conventional laser photocoagulation techniques may not offer optimal solutions to treating areas close to or with such sensitive tissue while ensuring that damage to such tissue will be avoided or greatly reduced. Further, treating relatively large areas such as the macular region with conventional techniques such as with a scanner or treating multiple smaller spots within the larger area may not provide optimal, sufficient, or uniform heating to treat the area and may result in additional loss of visual acuity. Accordingly, there is a need in the art for improved laser treatment methods and systems including subthreshold laser photoactivation or low energy, intracellular, sub-lethal and ophthalmoscopically invisible treatment of the retinal tissue including the retinal pigment epithelium within the macula region for diseases such as diabetic retinopathy, central serous retinopathy, and central and branch vein occlusions, among others. The common denominator for these diseases is swelling of the macula which causes a degradation of best corrected visual acuity. In particular, there remains a need for improved large spot laser treatment systems and methods for treating large areas or spots of the retina including the macular region. Further, it may be desirable to treat such a large spot with a high-powered, large beam laser such that the large spot may be treated uniformly without a scanner or otherwise treating multiple smaller spots within the large spot.

BRIEF SUMMARY

Embodiments of the invention described herein provide systems and methods for treating retina tissue and/or other areas of a patient's eye, in particular, large areas including the macula. Such procedures may be used to treat diabetic macular edema and/or other conditions of the eye. According to one aspect, a system for providing a therapeutic treatment to a patient's eye includes a treatment beam source configured to transmit a treatment beam along a treatment beam path, the treatment beam having an infrared wavelength and a power from 1 mW to 10 W or 1 W to 100 W. The system further includes a processor coupled to the treatment beam source, the processor being configured to direct the treatment beam onto retinal tissue of the patient's eye and deliver a series of pulses from the treatment beam onto the retinal tissue at a first treatment spot to treat the retinal tissue. The first treatment spot is 1 to 6 mm in diameter. The duration of each pulse may be sufficiently short to allow tissue cooling between pulses. This limits the temperature increase at the tissue and avoids inducing photocoagulation of the retina. In contrast to photocoagulation these effects may be visible by means of ophthalmoscopy, optical coherence tomography, fluorescein angiography or autofluorescence imaging. The series of pulses directed to the treatment spot may induce intracellular, sub-lethal damage of retinal pigment epithelial cells which in turn activates intracellular healing mechanisms, e.g. up-regulation of heat shock proteins, cytokines and growth factors. These mechanisms restore and improve retinal pigment epithelial function, reduction of macular swelling and improvement of best-corrected-visual acuity. In some embodiments, a duration of each pulse is sufficiently short so as to avoid inducing photocoagulation of the retinal tissue that results in visible tissue damage and the series of pulses directed to the treatment spot induces photoactivation of a therapeutic healing at the treatment spot.

In some embodiments, the treatment beam is configured to be directed onto the retinal tissue of the patient's eye to heat the tissue in a substantially uniform manner without being scanned. The treatment beam source may be a vertical-cavity surface-emitting laser. The treatment beam source may be configured to be located above the patient to transmit the treatment beam through the cornea and pupil in a generally downward direction toward the patient's retina such that the patient may be in a supine position during treatment. Further, the treatment beam may be configured to be directed onto 80 to 100% of the macular region. In some embodiments, the treatment beam heats the retinal tissue at the first treatment spot to a maximum temperature between 50 and 55 degrees C. In some embodiments, the treatment beam source may include a VCSEL array, the array comprising a set of laser-delivery elements (e.g., laser diodes) that are individually powered. In these embodiments, delivering the series of pulses to the treatment spot may include delivering, by the laser-delivery elements, a plurality of laser beams to a plurality of sub-spots within the treatment spot, wherein laser outputs of the laser-delivery elements are individually adjusted so as to ensure substantially uniform tissue heating at the treatment spot.

In certain embodiments, the system further includes an aiming beam source configured to transmit an aiming beam along an aiming beam path, the aiming beam having a visible wavelength and the aiming beam path extending non-coaxially relative to the treatment beam path and wherein the processor is coupled to the aiming beam source. The processor is configured to direct the aiming beam onto the retinal tissue of the patient's retina at the first treatment spot and define, via the aiming beam, a treatment boundary surrounding the first treatment spot such that the first treatment spot is disposed therein. The aiming beam source may include a vertical-cavity surface-emitting laser. The treatment boundary may include at least one of a ring or circular cross-section. The aiming beam may have a power under 1 mW. In certain embodiments, a convex lens is disposed between the patient and the aiming beam source configured to focus the aiming beam onto a concentric ring on the retinal tissue surrounding the treatment beam at the first treatment spot. The treatment beam source may be disposed between the convex lens and the aiming beam source. A concave lens may be disposed between the aiming beam source and the treatment beam source configured to diverge the aiming beam around the treatment beam source such that only a portion of the aiming beam is blocked by the treatment beam source.

According to another aspect, a method for providing a therapeutic treatment to a patient's retina is provided. The method includes delivering, via a laser beam, a therapeutic treatment to retinal tissue of the patient's eye. The delivered therapeutic treatment includes a treatment spot on the retinal tissue at an intensity below that which effects coagulative damage in order to minimize damage to the retinal tissue. The treatment beam is delivered at an infrared wavelength, a power from 100 mW to 10 W, and along a treatment beam path and the treatment spot ranging from 1 to 6 mm in diameter.

Conventional photocoagulation results in lethal damage by denaturing or unfolding proteins rendering them non-functional and results in visible burns to the retina. In some embodiments, the method further includes delivering a series of pulses from the treatment beam onto the retinal tissue at the treatment spot to therapeutically treat the retinal tissue, wherein a duration of each pulse is sufficiently short so photocoagulation of the retinal tissue is avoided. The series of pulses are directed to the treatment area wherein the duration of each pulse is sufficiently short to allow tissue cooling between pulses. This limits the temperature rise at the tissue and avoids inducing photocoagulation of the retina. In contrast to photocoagulation these effects are visible by means of ophthalmoscopy, optical coherence tomography, fluorescein angiography or autofluorescence imaging. The series of pulses directed to the treatment spot induces intracellular, sub-lethal damage of retinal pigment epithelial cells which in turn activates intracellular healing mechanisms, e.g. up-regulation of heat shock proteins, cytokines and growth factors. These mechanisms restore and improve retinal pigment epithelial function, reduction of macular swelling and improvement of best-corrected-visual acuity.

In some embodiments, the therapeutic treatment is delivered only to a single treatment spot on the retinal tissue. In some embodiments, the method further includes heating the tissue at the treatment spot in a substantially uniform manner without scanning the treatment beam. In some embodiments, the treatment beam source is a vertical-cavity surface-emitting laser.

In some embodiments, the method further includes delivering the therapeutic treatment via a generally downward treatment beam path toward the patient's eye such that the patient may be in a supine position during treatment. In some embodiments, the first treatment spot includes a macular region of the retinal tissue. In some embodiments, the method further includes delivering the therapeutic treatment onto 80 to 100% of the macular region. In certain embodiments, the method further includes heating the retinal tissue at the first treatment spot to a maximum temperature between 50 and 55 degrees C.

In some embodiments, the method further includes delivering an aiming beam from an aiming beam source along an aiming beam path, the aiming beam having a visible wavelength and the aiming beam path extending non-coaxially relative to the treatment beam path, directing the aiming beam onto the retinal tissue of the patient's eye at the first treatment spot, and defining, via the aiming beam, a treatment boundary surrounding the first treatment spot such that the first treatment spot is disposed therein.

In some embodiments, the aiming beam source is a vertical-cavity surface-emitting laser. In some embodiments, the treatment boundary includes at least one of a ring or circular cross-section. In certain embodiments, the aiming beam has a power under 1 mW.

In some embodiments, directing the aiming beam onto the retinal tissue includes directing the aiming beam through a convex lens disposed between the patient and the aiming beam source to focus the aiming beam onto a concentric ring on the retinal tissue surrounding the first treatment spot. The treatment beam source may be disposed between the convex lens and the aiming beam source. Directing the aiming beam onto the retinal tissue may include directing the aiming beam through a concave lens disposed between the aiming beam source and the treatment beam source to diverge the aiming beam around the treatment beam source such that only a portion of the aiming beam is blocked by the treatment beam source prior to directing the aiming beam through the convex lens.

In accordance with another aspect of the invention, a system for providing a therapeutic treatment to a patient's eye is provided that includes an aiming beam source configured to transmit an aiming beam along an aiming beam path and a treatment beam source configured to transmit a treatment beam along a treatment beam path extending non-coaxially relative to the aiming beam path. The system includes a convex lens disposed between the patient and the treatment beam source, a concave lens disposed between the treatment beam source and the aiming beam source, and a processor coupled to the aiming beam source and the treatment beam source. The processor is configured to direct the aiming beam through the concave lens configured to diverge the aiming beam around the treatment beam source such that only a portion of the aiming beam is blocked by the treatment beam source prior to directing the aiming beam through the convex lens configured to focus the aiming beam onto retinal tissue of the patient's eye to define a visible treatment boundary on the retinal tissue. The processor is configured to direct the treatment beam onto retinal tissue of the patient's eye at a first treatment spot disposed within the treatment boundary formed by the aiming beam.

In accordance with another aspect of the invention, a method for providing a therapeutic treatment to a patient's eye is provided that includes delivering an aiming beam from an aiming beam source along an aiming beam path, the aiming beam passing through a concave lens disposed between the patient and the aiming beam and configured to diverge the aiming beam around a treatment beam source such that only a portion of the aiming beam is blocked by the treatment beam source prior to passing through a convex lens disposed between the patient and the treatment beam source. The method includes defining, via the aiming beam, a visible treatment boundary on retinal tissue of the patient, the aiming beam passing through the convex lens to be focused onto the retinal tissue to define the treatment boundary. The method further includes delivering, via a treatment beam from the treatment beam source, a therapeutic treatment to retinal tissue of the patient's eye at a treatment spot on the retinal tissue disposed within the treatment boundary, the treatment beam being delivered along a treatment beam path extending non-coaxial relative to the aiming beam path.

In accordance with another aspect of the invention, a method for providing a pre-treatment evaluation of an eye of a patient. One or more steps of the method may be performed by one or more processors. The method includes receiving initial electroretinography (ERG) data from one or more ERG sensors (e.g., electrodes) positioned on a patient. The method may include positioning a first ERG sensor on a forehead of the patient, and positioning a second ERG sensor below the eye. One or more first pulses of an optical beam may be delivered toward a retina of the eye, wherein the first pulses are set to a first power. First ERG data from the ERG sensors may be received, wherein the first ERG data reflects measured ERG signals generated by retinal cells as a response to the first pulses. One or more optimal laser power values may be determined for performing a laser treatment. The first pulses may be delivered to a first treatment spot on the retina, the first treatment spot being 1 to 6 mm in diameter.

In some embodiments, the initial ERG data may reflect a baseline ERG signal. In other embodiments, the method includes delivering one or more initial pulses of an optical beam toward the retina, in which case the initial ERG data may reflect measured ERG signals generated by retinal cells as a response to the initial pulses.

In some embodiments, the method includes performing first least-squares fits on the initial ERG data and the first ERG data to generate respective waveforms corresponding to the initial ERG data and the first ERG data. In some embodiments, the method includes performing a second least-squares fit on the waveforms generated by the first least-squares fits, wherein the second least-squares fit is configured to generate a linear representation based on the waveforms generated by the first least-squares fits, wherein the line describes the relationship between retinal temperature and laser power values. The linear representation may be characterized by the equation $C=X\beta+\varepsilon$, where C is retinal temperature, X is a power value for the treatment laser, $\beta$ is a regression coefficient, and c is an error term. In some embodiments, the method includes generating a lookup table that correlates laser power values to ERG signal data or retinal temperatures.

In some embodiments, the method includes delivering, by a treatment beam source, one or more treatment laser beams to a first treatment spot on the retina, wherein the first treatment spot is 1 to 6 mm in diameter, and wherein the treatment beam source is set to one of the optimal laser power values. In some embodiments, the treatment beam source includes a vertical-cavity surface-emitting laser (VCSEL) array, the array comprising a set of laser-delivery elements that are individually powered. In some embodiments, delivering the one or more laser beams to the first treatment spot includes delivering, by the laser-delivery elements, a plurality of laser beams to a plurality of sub-spots within the first treatment spot, wherein laser outputs of the laser-delivery elements are individually adjusted so as to ensure substantially uniform tissue heating at the treatment spot.

In some embodiments, the method includes delivering one or more second pulses of an optical beam toward the retina of the eye, wherein the second pulses are set to a second power. The method includes receiving second ERG data from the ERG sensors, wherein the ERG data reflects measured ERG signals generated by retinal cells as a response to the second pulses. First least-squares fits may be performed on the initial ERG data, the first ERG data, and the second ERG data to generate respective waveforms corresponding to the initial ERG data, the first ERG data, and the second ERG data. A second least-squares fit may be performed on the waveforms generated by the first least-squares fit, wherein the second least-squares fit is configured to generate a linear representation based on the waveforms generated by the first least-squares fits, wherein the linear representation describes the relationship between retinal temperature and laser power values.

BRIEF DESCRIPTION OF THE DRAWINGS

FIG. 7 and FIG. 8 are flowcharts illustrating example therapeutic treatment processes.

DETAILED DESCRIPTION

Embodiments of the present invention described herein provide systems and methods for treating retina tissue and/or other areas of a patient's eye, in particular, large areas including the macula. Such procedures may be used to treat diabetic macular edema and/or other conditions of the eye to induce one or more therapeutic benefits. In some embodiments, a series of short duration light pulses (e.g., between 5-30 microseconds, 10-30 microseconds, or 5-15 microseconds) may be delivered to the retinal tissue with a thermal relaxation time delay between each pulse to limit the temperature rise of the target retinal tissue and thereby limit a thermal effect to only the retinal pigment epithelial layer. Short duration pulse treatments, such as MicroPulse™ Laser Therapy of systems and devices sold by IRIDEX® Corporation (hereinafter short duration pulse treatments of procedures), may not result in visible spots that appear on the retina and may result in less or no overall tissue damage (e.g., visible damage). In other embodiments, photocoagulation may result in a series of visible spots that do appear in the retina.

Figure 1:
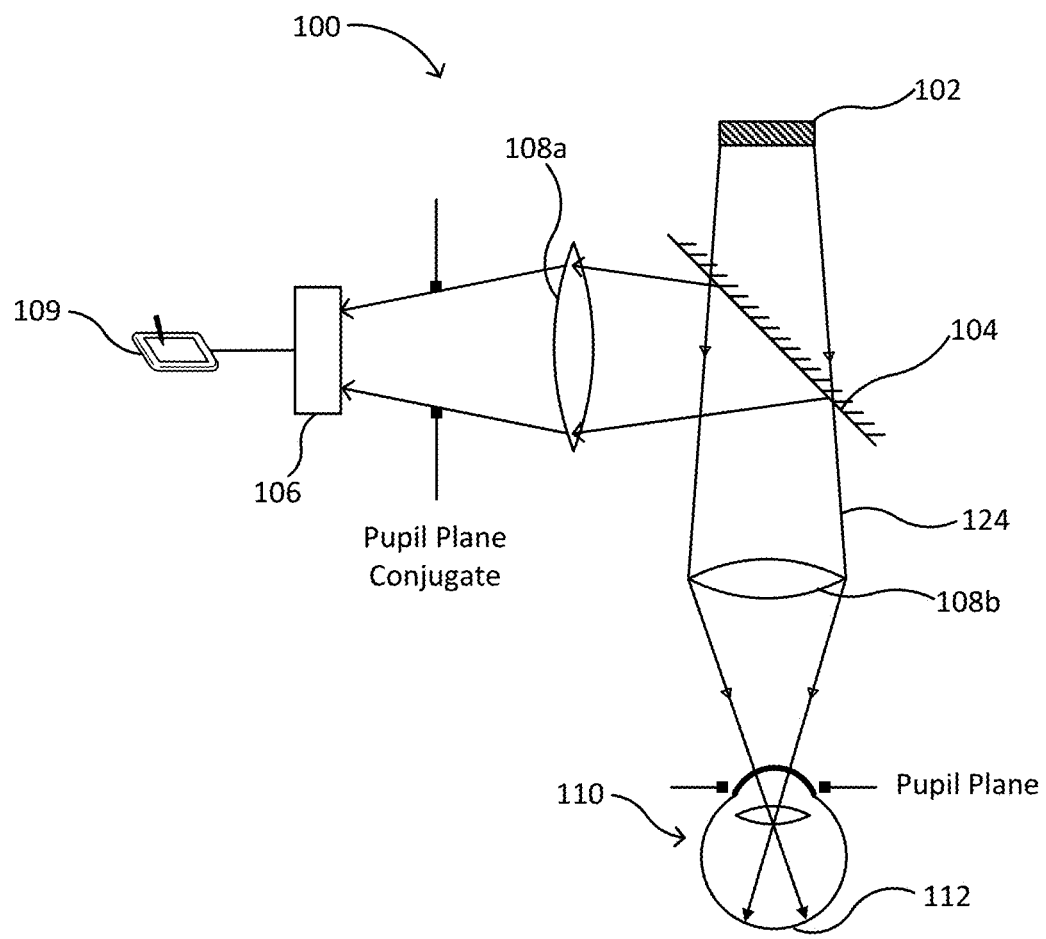
FIG. 1 is a schematic illustration of a laser treatment system for providing large spot therapeutic treatments in accordance with an embodiment of the present invention.

FIG. 1 illustrates a high-level schematic of a laser delivery system 100 for delivering a treatment beam to a patient's eye 110. With reference to FIGS. 1-5, a laser delivery instrument or laser treatment system 100 as described herein includes a treatment beam source 102 (e.g., a laser delivery source) such as a laser diode (e.g., a vertical-cavity surface-emitting laser "VCSEL") configured to transmit a treatment beam or laser along a treatment path 124. In some embodiments, the laser treatment system 100 may be adapted to accept a VCSEL diode in order to significantly reduce costs associated with the laser treatment system (VCSEL diodes may be significantly cheaper than other alternatives). The treatment beam source 102 may be aligned with a mirror 104 for passing or reflecting the treatment laser with low loss toward a target treatment spot or area of a patient's eye 110 to be treated (e.g., macula 112). Mirror 104 may be a perforated mirror, half mirror, dichroic mirror, and the like. Mirror 104 may be transparent or semi-transparent so that some light (e.g., illumination light or aiming laser) may be delivered back to a camera 106 as described herein. Camera 106, treatment beam source 102, or an aiming beam source may be operably coupled to a computer 109 (e.g., computing system, controller) to provide retinal mapping, tracking, and/or imaging that may be used in the therapeutic treatment processes described herein or to control delivery of the treatment laser or an aiming laser. One or more lenses (e.g., identified individually as lens 108a and lens 108b) may be provided to focus the reflected or passed light or laser to a target position (e.g., the camera 106 and/or patient's eye 110). For example, lenses 108a and 108b may be convex lenses.

While components of the laser treatment system 100 are illustrated separately or externally in FIG. 1, one or more of the components (e.g., the treatment beam source 102) may be integrated or packaged together internally (e.g., within a housing of an adapter) or coupled to the adapter (e.g., via an optical fiber). The adapter or one or more of the components may be coupled with a slit lamp or other ophthalmic imaging instrument. Examples of laser delivery instruments or other various components including an adapter, controller, computer, or processor, as described herein that may be provided with laser treatment system 100, in whole or in part, are described in U.S. Pat. No. 9,707,129, the full disclosure of which is incorporated herein by reference in its entirety for all purposes.

In some embodiments, the treatment beam source 102 or an aiming source as described in more detail below may also include a computing device and/or processor operably coupled to the computer 109 or other external or internal controller to route information between the computer 109 and beam source 102 or aiming source such that the computer 109 may control delivery of the treatment laser or an aiming laser. Computer 109 may include a separate or integrated display interface including controls and a display to display various settings and/or operations that may be adjusted by a clinician. For example, computer 109 may control treatment beam source 102 to deliver the treatment laser onto a target location of the patient's eye with desired treatment parameters or dosimetry as described in more detail below. Treatment laser may be controlled to be delivered within a defined treatment boundary, with a laser density or intensity, power, wavelength, and/or duration or pulse to treat a target location of a specified size.

In some embodiments, the treatment laser may be controlled or delivered to treat single, large target spots (e.g., macula), positions, or locations with diameters from 1-6 mm (e.g., above 5 mm) and heat the spots uniformly (e.g., without a scanner or treating multiple smaller spots within the large spot). Such large spots may be treated with short duration, high powered pulses from 10 mW to 10 W, 100 mW to 10 W, or from 1 W to 100 W (e.g., 3 W, 4 W, 5 W, above 2 W, above 5 W). Further, a duration of each pulse may be sufficiently short so as to avoid inducing traditional photocoagulation of the retinal tissue, but may be sufficient to induce photoactivation or therapeutic healing substantially uniformly at each target position, spot, or location. In some embodiments, the pulses may induce low energy, intracellular, sub-lethal and ophthalmoscopically invisible treatment of the retinal tissue including the retinal pigment epithelium within the macula region for diseases such as diabetic retinopathy, central serous retinopathy, and central and branch vein occlusions, among others. In some embodiments, tissue at the target location may be heated in a range or up to a maximum temperature from 50 to 55 degrees C. such that photoactivation or low energy, intracellular, sub-lethal and ophthalmoscopically invisible treatment is induced while avoiding or reducing the permanent retinal damage resulting from traditional photocoagulation. Treatment laser may have a wavelength selected within the infrared spectrum (e.g., 808 nm, 810 nm). In certain embodiments, the treatment laser may be delivered to target locations to prophylactically treat the patient's eye.

Figure 2A:
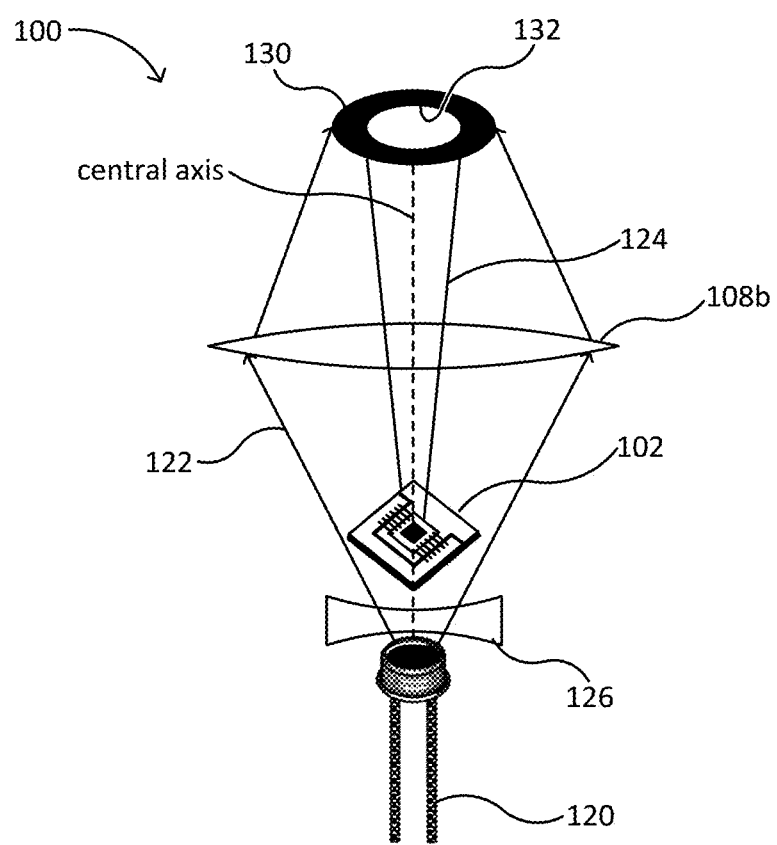
FIG. 2A illustrates a laser delivery system with an aiming beam source.

FIG. 2A illustrates a laser delivery system 100 with an aiming beam source 120. Referencing FIG. 2, in some embodiments, the laser delivery system 100 may include an aiming beam source 120 such as a laser diode (e.g., a vertical-cavity surface-emitting laser "VCSEL") operably coupled to computer 109 configured to transmit an aiming beam or laser along an aiming path 122. In some embodiments, the aiming path 122 may not be aligned or substantially co-axial with treatment path 124. In some embodiments, aiming path 122 may be aligned or substantially co-axial with treatment path 124, as illustrated in FIG. 2. In some embodiments, as illustrated in FIG. 2, the treatment beam source 102 may be positioned in front of or closer to the patient's eye in the path of aiming beam source 120 such that the aiming path is partially blocked. A concave lens 126 may be positioned between the aiming beam source 120 and treatment beam source 102 to expand or diverge the aiming laser such that the aiming path 122 is only partially blocked by the treatment beam source 102. A convex lens (e.g., convex lens 108b) may be positioned or disposed between the treatment beam source 102 and patient's eye 110 to focus or converge the aiming beam or treatment beam onto the target or treatment spot on the patient's eye 110.

As illustrated, the convex lens focuses the aiming beam onto a concentric aiming ring 130 that surrounds the treatment beam at the treatment spot on the patient's eye such that the aiming beam is always larger than the treatment beam (e.g., an incident spot 132 of treatment beam source 102). The aiming beam may have a wavelength in the visible spectrum (e.g., 600 nm, 650 nm, 700 nm) to provide a visible treatment boundary (e.g., a concentric ring, solid circular spot, or other geometric shape) on the patient's retina with a power at or under 1 mW. The treatment boundary provided by the aiming beam provides a safety margin for laser treatment of the eye. The treatment boundary defines an area or periphery within which therapeutic treatment by the treatment beam will be or can be provided and outside which therapetuci treatment is not provided. Further, treatment boundary provided by the aiming beam may be positioned adjacent tissue of the retina for which a therapeutic treatment is not desired (e.g., sensitive or non-target tissue). The tissue not to be treated falls outside the treatment boundary and is visible to a clinician. This allows the clinician to position the treatment boundary as close to or distant from such tissue as desired while ensuring that such tissue is not treated. The treatment beam is configured within the aiming ring or treatment boundary to ensure that tissue outside the treatment boundary is not treated accordingly.

Figure 2B:
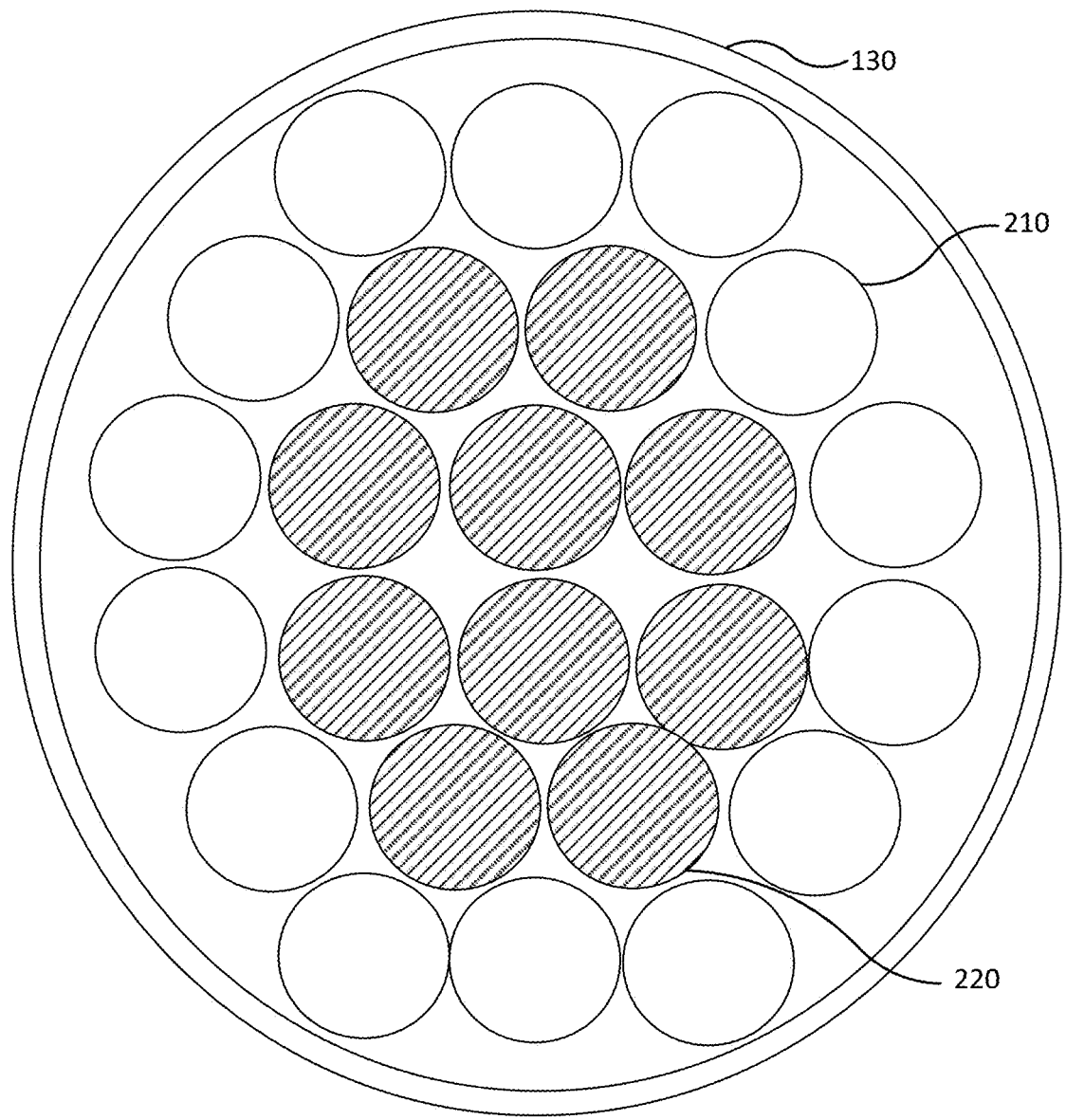
FIG. 2B illustrates an example of a treatment beam that includes a plurality of sub-spots within an aiming ring, wherein the treatment beam is generated by a treatment source comprising a plurality of corresponding laser-delivery elements.

FIG. 2B illustrates an example of a treatment beam that includes a plurality of sub-spots (e.g., the sub-spot 210 and the sub-spot 220) within an aiming ring 130, wherein the treatment beam is generated by a treatment source 102 comprising a plurality of corresponding laser-delivery elements (e.g., an array of laser diodes). In some embodiments, the treatment laser-delivery elements may be individually powered to allow for fine-tuned adjustments in delivering a desired energy distribution. For example, each laser-delivery element in an array may be controlled individually (e.g., by separately controlling the pulse duration, frequency, power, etc. of each laser-delivery element) to cause uniform tissue heating over a region defined by the large spot. Such control may be necessary for uniform tissue heating, because for example, when laser-delivery elements in an array fire beams of identical parameters toward an array of corresponding adjacent sub-spots, the tissue areas in the vicinity of the interior sub-spots toward the center of the array of sub-spots (e.g., the sub-spot 220), may be heated more than the tissue areas in the vicinity of the exterior sub-spots toward the periphery of the array of sub-spots (e.g., the sub-spot 210). This is due to the fact that the tissue areas near the interior sub-spots may be exposed to and therefore accumulate compounded energy from a larger number of surrounding sub-spots than the tissue areas near the exterior sub-spots. The parameters of each of the sub-spots may be adjusted to control for these differences in energy exposure. For example, the treatment system may supply a relatively low level of energy via the treatment laser-delivery elements corresponding to the interior sub-spots when compared to the level of energy supplied via the treatment laser-delivery elements corresponding to the exterior sub-spots. As another example, the treatment system may deliver more precise uniformity by fine-tuned control of each of the sub-spots (e.g., varying them to account for other variables such as tissue density). In some embodiments, subsets of the treatment laser-delivery elements may be powered together as groups and thereby controlled separately for similar reasons. For example, a 10×10 array may be divided into 10 subsets of 10 elements. In this example, each of the 10 subsets may be powered separately.

Figure 3:
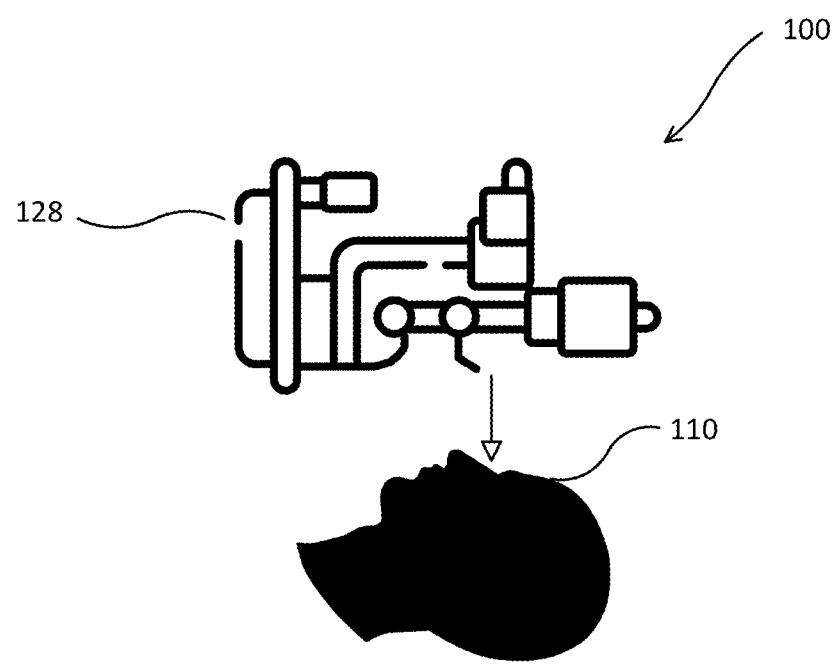
FIG. 3 is an illustration of the laser treatment system of FIG. 1 in accordance with yet another embodiment of the present invention.

FIG. 3 illustrates an example of the laser treatment system 100 in use on a patient. In some embodiments, as illustrated in FIG. 3, the patient may be treated with the laser treatment system 100 while in a supine position. In such embodiments, one or more of the components of the laser treatment system 100 may be operably coupled to a slit lamp 128, or other ophthalmic imaging system or laser delivery instrument as described herein such that the treatment beam path is directed downward onto the patient's eye. For example, a conventional slit lamp or other ophthalmic imaging instrument may be rotated about 90 degrees from a conventional position that directs the treatment into a patient's eye in a sitting position. Vertically aligning an optical axis or treatment path of the treatment beam source 102 improves controllability of distance between the treatment laser and patient's eye. Additionally, this allows for better treatment outcomes in patients, because it reduces patient head movement (e.g., by decreasing the degrees of freedom available to a patient) that may result in improper targeting of the treatment beam during a given treatment duration. This may be particularly advantageous in treating children or adults with difficulty sitting still. In some embodiments, the slit lamp or other instrument may be coupled to a ceiling or other fixture above the patient or operating table (e.g., an IV pole or support bar). In some embodiments, additional drugs or medication may be provided during treatment of the eye (e.g., when coupled to an IV pole).

Figure 4A:
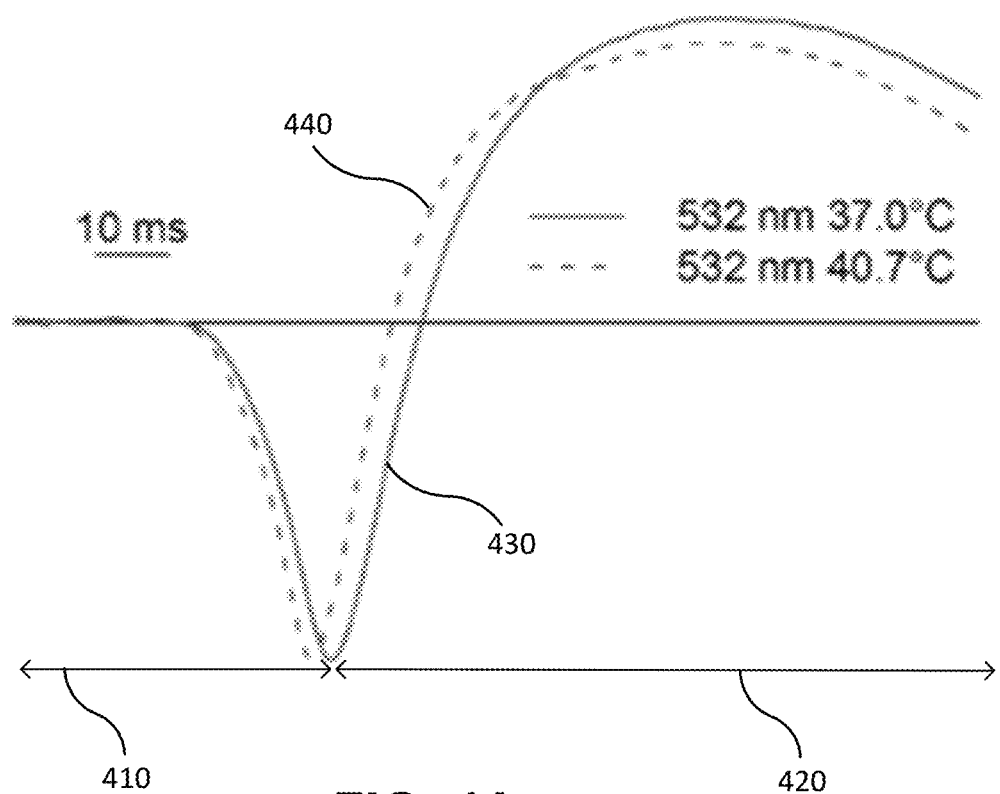
FIG. 4A illustrates an example electroretinography (ERG) recordings of a mouse retina.
Figure 4B:
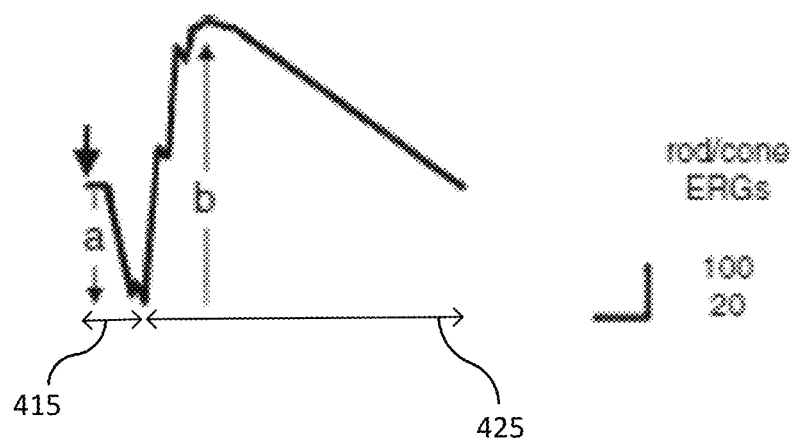
FIG. 4B illustrates an example ERG recording of a human retina.

FIG. 4A illustrates an example electroretinography (ERG) recordings of a mouse retina. ERG measures voltages (or biopotentials) of an electrical signal generated by photoreceptors of a retina when they receive an excitatory stimulus such as light (e.g., from a light source such as a laser). In some embodiments, ERG may be a noninvasive technique that records an average of these generated voltages using, for example, one or more skin-mounted sensors (e.g., electrodes). The ERG recording illustrated in FIGS. 4A-4B depict voltages measured as a light source (e.g., a laser) is shined on a retina. ERG has been conventionally employed to measure retinal response to stimuli such as flashing patterns. More information about using ERG to measure retinal response to such external stimuli may be found in U.S. Pat. Nos. 4,874,237, 5,154,174, and 9,026,189, which are hereby incorporated by reference herein in their entirety. A recent study on mice showed that ERG signals may be temperature dependent in mice retinas, such that retinal temperature of mice subjected to a laser may be inferred by a measured ERG signal. The results of this study are published in a paper—Marja Pitkanen et al., "A Novel Method for Mouse Retinal Temperature Determination Based on ERG Photoresponses," *Ann. Biomed. Eng., Vol.* 45, No. 10, Oct. 2017—which is incorporated herein by reference in its entirety. The ERG in FIG. 4A depicts waveforms reflecting mouse retinal ERG measurements taken at a 10 ms interval for retinal temperatures of 37.0 degrees C. and 40.7 degrees C. when a 532 nm laser beam is fired at a mouse retina. The electrical signal generated by the body typically results in a waveform that includes two distinct waves: an a-wave 410 and a b-wave 420. As shown in FIG. 4A, the ERG waveforms 430 and 440 measured while at the two retinal temperatures (37.0 degrees C. and 40.7 degrees C., respectively) are consistently different, indicating that the waveforms are temperature-dependent. As such, the waveforms may be used to infer retinal temperatures.

FIG. 4B illustrates an example ERG recording of a human retina, excerpted from Quinteros Quintana et al., "Electroretinography: A Biopotential to Assess the Function/Dysfunction of the Retina," *J. Phys.: Conf. Ser.* 705 (2016), which is incorporated herein by reference in its entirety. The inventors of this disclosure observed that the ERG recording of the human retina illustrated in FIG. 4B is very similar to the ERG recording of the mouse retina illustrated in FIG. 4A. For example, the a-wave 415 maps onto the a-wave 410, and the b-wave 425 maps onto the b-wave 420. This correlation led the inventors of this disclosure to conceive of the idea of using ERG recordings to infer human retinal temperature, and leveraging this property to determine treatment parameters for laser treatments as disclosed herein. Conventional techniques for determining treatment parameters includes slowly titrating upward the power of a laser beam source until a visible burn spot is observed on the retina to determine a maximum power value limit. Such techniques inevitably cause a level of damage to the retina even when performed correctly, which may have undesirable effects. By its very nature, targeting the retina with a laser beam without having established a maximum power value limit comes with the risk of temporary or even irreversible damage. Additionally, the conventional techniques require subjective judgments from operators that must be informed by extensive experience and skill to determine the maximum power value limit. Finally, assessing thresholds using these conventional techniques requires additional time and effort on the part of the practioner. The present disclosure describes the use of an ERG measurement system for use in conducting pre-treatment measurements for a retina in a manner so as to address the deficiencies of the conventional titration techniques.

Figure 5:
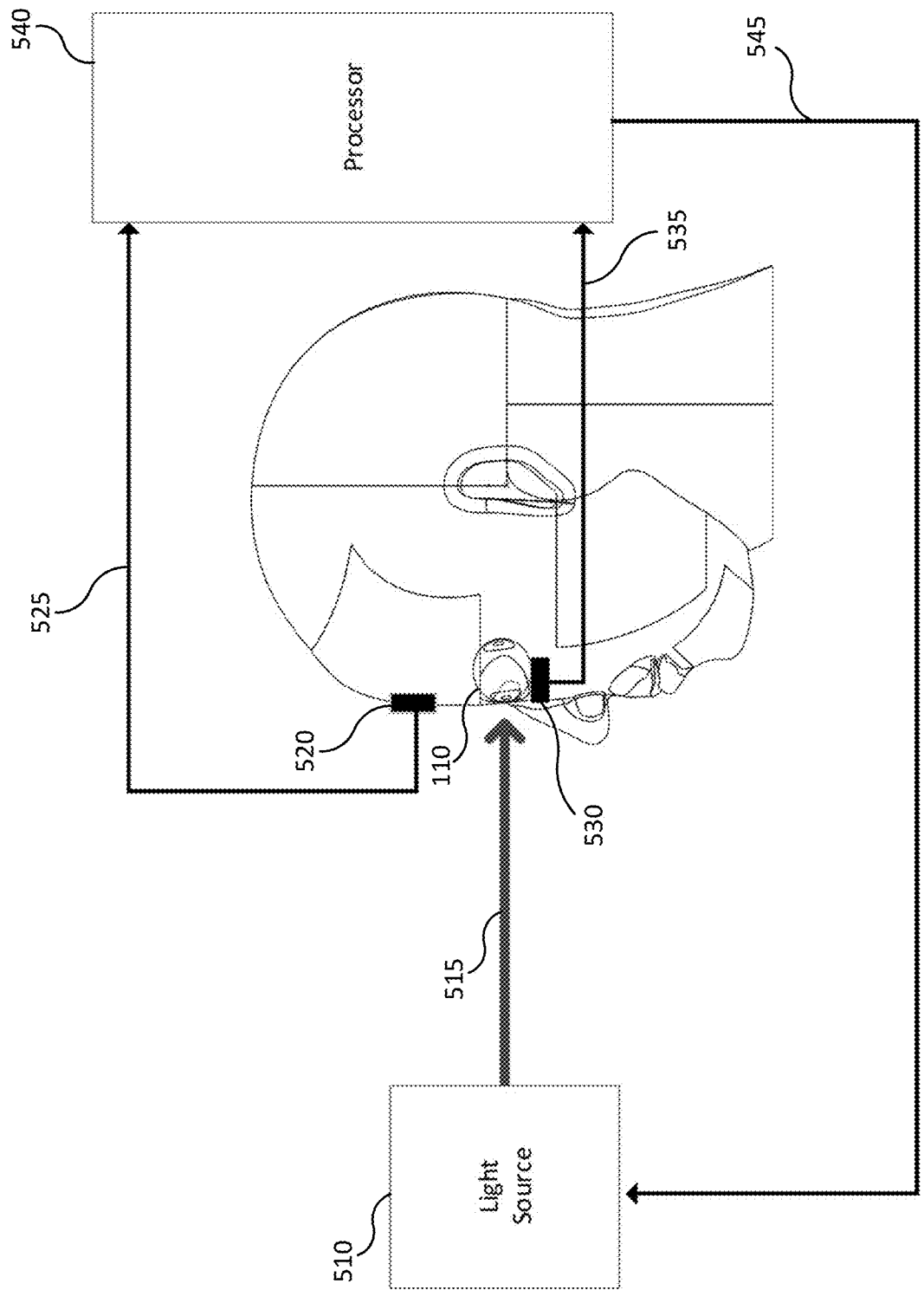
FIG. 5 illustrates an example configuration of an example ERG measurement system.

FIG. 5 illustrates an example configuration of an example ERG measurement system. The illustrated ERG measurement system includes a light source 510 that is configured to aim an optical beam 515 toward an eye 110 of a patient. In some embodiments, the light source 510 may be a laser that is configured to emit a beam having a suitable wavelength (e.g., 532 nm, 577 nm, 810 nm). In some embodiments, the ERG measurement system includes at least two sensors (e.g., electrodes) for measuring a voltage generated by photoreceptors in response to the optical beam 515. For example, as illustrated in FIG. 5, the ERG measurement system may include a first sensor 520 that is positioned on a forehead of the patient and a second sensor 530 that is positioned below the eye 110 of the patient. These first and second sensors 520 and 530 may be secured to the patient via a suitable securing mechanism (e.g., adhesive patches). A conductive cream or gel may be applied between each sensor and the patient to allow for better ERG signal acquisition. The first and second sensors 520 and 530 may be coupled to a processor 540 (e.g., via a wired or wireless connection) as illustrated by the arrows 525 and 535, respectively. The processor 540 may perform one or more operations as described herein to intelligently determine a model that predicts correlations between power of the treatment laser and temperature. For example, the processor 540 may generate a prediction model that predicts a correlation between the power of the optical beam 515 and retinal temperature. This prediction model may be used to predict a power that is necessary to increase a retinal temperature to a desired amount, and/or a maximum power value limit that is configured to raise retinal temperature to the highest amount possible without causing undue damage (e.g., in direct contrast with conventional techniques which may make use of visible burn spots as a routine part of the technique) to the retina. In some embodiments, the processor 540 may be coupled (e.g., via a wired or wireless connection) to a display or other interface that indicates these predictions to an operator (e.g., an interface that display a power range depicting the minimum and maximum power values for the optical beam 515). In some embodiments, the processor 540 may be coupled (e.g., via a wired or wireless connection) to the light source 510 (as illustrated by the arrow 545) such that the processor may be used to control the power of the light source 510. In these embodiments, the processor 540 may cause the light source 510 to direct multiple optical beams 515 of different power values (e.g., referencing FIG. 6, a minimum power value at step 620 and the higher power at step 635) at the eye 110 to collect multiple ERG measurements and refine the prediction model.

ERG measurements may be particularly suitable for treatments involving large spot treatments. In some embodiments, the measurable ERG response may be a large electrical ERG signal generated by a large number of retinal cells. Large spot treatments may be particularly suitable for these measurements, because they stimulate a large number of retinal cells simultaneously and thereby recruit a larger and therefore more measurable ERG response.

Figure 6:
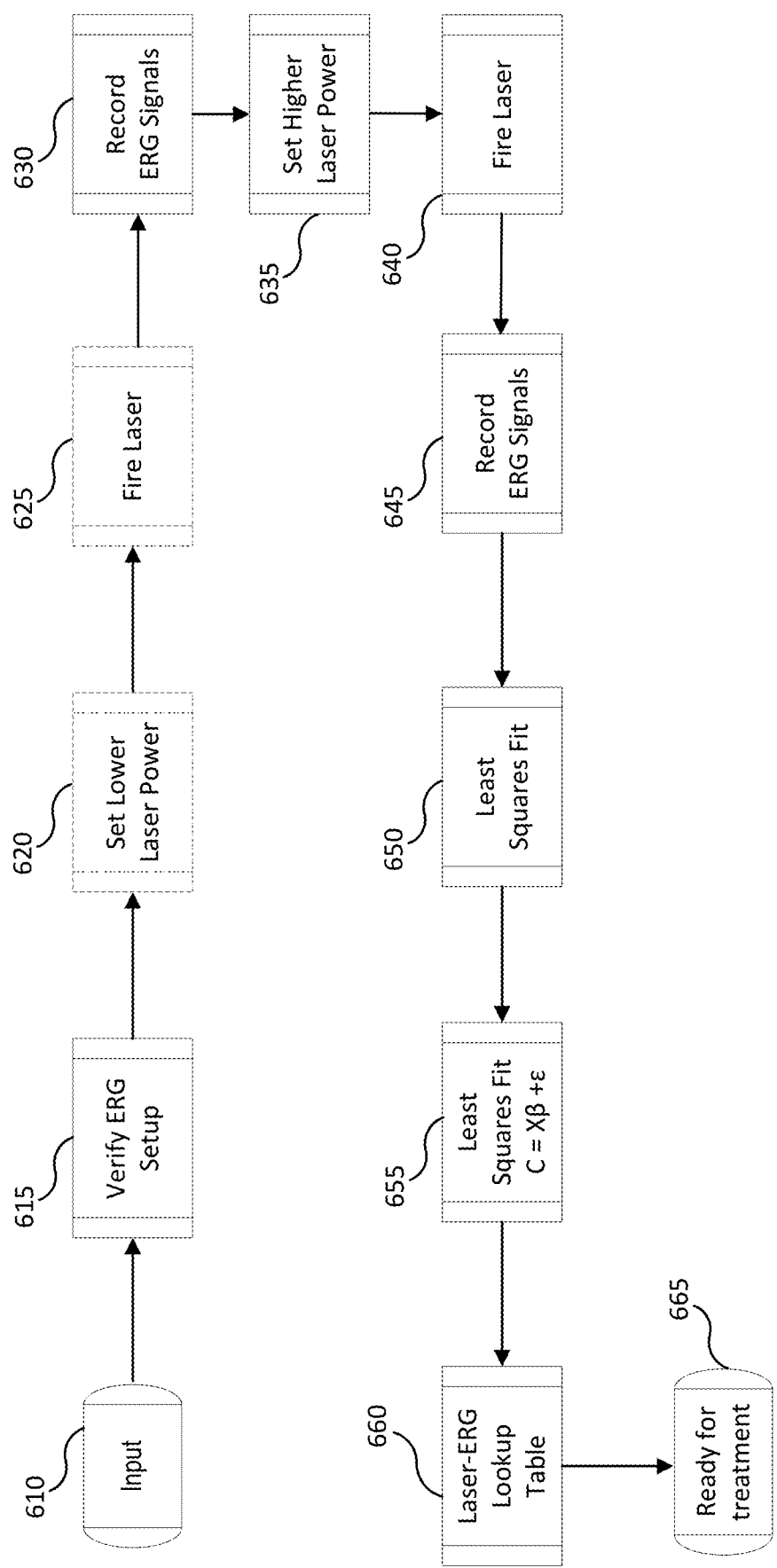
FIG. 6 illustrates an example process for creating a prediction model that may be generated prior to treatment

FIG. 6 illustrates an example process for creating a prediction model that may be generated prior to treatment (e.g., referencing FIG. 5, by the processor 540). In some embodiments, the process may begin with an input 610 (e.g., by the operator) to begin pre-treatment assessment of a patient eye. In some embodiments, a processor may verify that the ERG sensors and other hardware are set up correctly (e.g., by verifying baseline signatures received from ERG sensors), as illustrated in step 615. At step 620, a laser source (or other light source) may be set to a minimum power value. At step 625 the treatment laser may be fired at a relatively low power (e.g., the minimum laser power value). In some embodiments, the steps 620 and 625 may be skipped. At step 630, ERG signal data may be recorded (e.g., during or immediately following the firing of the treatment laser in step 625) using sensors placed on a patient. These recorded ERG signal data may correspond to electrical responses generated by retinal cells in response to the treatment laser at its minimum power value (or at some other relatively low power). In embodiments where step 620 and 625 are skipped, this ERG waveform may reflect signals detected when the eye is exposed to, for example, ambient light in which case the retinal temperature may be a baseline temperature (e.g., 37 degrees C.). At step 635, the treatment laser may be set to a higher power (e.g., 1 W). This higher power may be beneath an expected maximum power value limit at which damage to the retina may occur. At step 640, the treatment laser may be fired at the higher power. At step 645, ERG signal data may be recorded again (e.g., during or immediately following the firing of the treatment laser in step 635), this time corresponding to electrical responses generated by retinal cells in response to the treatment laser at the higher power. In some embodiments, the ERG waveforms may be translated from analog ERG signal data to digital waveforms. At step 650, a processor may be used to perform a least-squares fit on the ERG signal data recorded at steps 630 and 645. The least-squares fit may be performed to generate, based on the measured ERG signal data, waveforms similar to the waveform depicted in FIG. 4B. For example, the least-squares fit may generate a waveform corresponding to the lower-power (or baseline) ERG signal data recorded at step 630, and also a waveform corresponding to the higher-power ERG signal data recorded at step 645. At step 655, a further these scores fit may be performed to linearize the waveform outputs of step 650 and thereby describe a relationship between retinal temperature and a laser power value. For example, step 655 may linearize the waveform outputs to generate a linear representation (e.g., a single line) described by, e.g., the equation $C=X\beta+\varepsilon$, where C is retinal temperature, X is a power value for the treatment laser, $\beta$ is a regression coefficient, and $\varepsilon$ is an error term. At step 660, a lookup table may be generated based on the linear equation of step 655. The lookup table may correlate retinal temperatures to power values of the treatment laser such that an operator may be able to predict a retinal temperature that may be achieved by firing a laser at a particular power. In some embodiments, any or all of the steps outlined in FIG. 6 may be performed automatically by one or more processors. Although FIG. 6 illustrates only two ERG measurements, the disclosure contemplates embodiments where any suitable number of ERG measurements are performed (e.g., a series of ERG measurements performed sequentially with gradually increasing a power value of the laser). In some embodiments, a system may leverage a machine learning model that may have been trained using a large data set from a pool of subjects to generate more accurate prediction models. The subjects may be human patients, or alternatively may be animal subjects such as mice whose a-waves and b-waves may be correlated with a baseline ERG measurement of a particular human patient to assist in generating a lookup table for the particular human patient.

At step 665 of FIG. 6, a laser system 100 may be made ready for treatment. An operator may consult the lookup table to determine one or more optimal power values for delivering a treatment beam to a treatment spot (e.g., a treatment spot having a diameter between 1 mm and 6 mm). As discussed previously herein, in some embodiments, the treatment beam source may comprise a plurality of laser-delivery elements (e.g., a plurality of laser diode) that correspond to a plurality of sub-spots that come together to create the treatment spot. Also as discussed previously herein, in these embodiments, the laser output of each laser-delivery element (or subsets of the laser-delivery elements) may be controlled separately and adjusted (e.g., to ensure uniform heating). In these embodiments, when an operator sets the treatment beam source at a particular power, the laser system 100 powers each laser-delivery element to deliver laser beams such that the sum of the power values delivered by the plurality of laser-delivery elements is equal to or approximately equal to the particular power that the operator sets. A VCSEL array (or similar arrays) may be particularly advantageous in that it may allow for individual control of each laser-delivery element.

Using ERG measurements as described in the above-described process may render it unnecessary for operators to rely (or solely rely) on more conventional techniques that involve titrating a power value of the treatment laser upward to a maximum power value limit—for example, to a point where a visible burn mark is created (e.g., thereby indicating the maximum power value limit). Instead, operators may use lasers at power levels well within a safe range to predict the effects on the eye at different power levels including at the maximum power value limit. Effectively, predictions based on the ERG signal can be a substitute for a burn mark and may be recorded as suc, and processed by software. The result is a safer pre-treatment measurement (e.g., not requiring creation of visible burn marks) as compared to conventional titration techniques. Moreover, the ERG measurement process provides reliable measurements of temperature by measuring retinal cellular responses directly such that errors associated with other types of noninvasive measurements that rely on indirect measurements (e.g., measurement of acoustic waves that are created by the pulsed laser heating of the retina that must rely on an acoustic signal that propagates through several variable acoustic impedances). In addition, contrary to conventional techniques, the described ERG pre-treatment measurement process does not require the extensive experience and skill to make subjective judgments. The describe ERG pre-treatment measurement process may also be more accurate and of higher sensitivity that conventional techniques, because it does not rely on subjective judgments (thereby eliminating or reducing the possibility of human error). Finally, the described ERG measurement process does not require the same degree of time and effort on the part of the practioner as do conventional titration techniques.

In some embodiments, the ERG measurement system may be used during treatment of the retina to provide feedback (e.g., continuous or semi-continuous feedback) to the operator. For example, as treatment is ongoing, real-time ERG measurements may be taken and retinal temperatures may be determined (e.g., using a lookup table generated as described above during pre-treatment) and displayed to the operator to ensure that the retinal temperatures do not exceed an upper limit that would cause permanent damage.

In some embodiments, the laser treatment system may include alarm system to assist the operator in preventing permanent damage. For example, the alarm system may be coupled to the ERG measurement system, and when feedback data from the ERG measurement system is used to determine that retinal temperatures are within a threshold of the upper limit, the alarm system may generate an alarm notification or may even prevent operation of the treatment laser (e.g., by disabling a foot switch or other means of operating the treatment laser). In some embodiments, the laser treatment system may include an alarm system for ensuring that all required conditions are met before a treatment can be started. For example, the prediction model derived from the ERG measurement system may specify that a treatment laser is to be limited to a maximum power value limit of 3 W. In this example, if an operator were to adjust the treatment laser to a power of 4 W, the alarm system may generate an alarm notification or may prevent operation of the treatment laser.

FIGS. 7 and 8 illustrate exemplary methods 700 and 800 for providing a therapeutic treatment to a patient's eye. One or more of any steps of methods described herein may be removed, re-ordered, substituted, added, or modified. At step 702, a therapeutic treatment may be delivered, via a treatment beam from a treatment beam source, to retinal tissue of the patient's eye 702. The delivered therapeutic treatment may include a treatment spot on the retinal tissue at an intensity below that which effects coagulative damage so as to minimize damage to the retinal tissue. The treatment beam is delivered at an infrared wavelength, a power from 1 to 100 W, and along a treatment beam path and the treatment spot ranges from 1 to 6 mm in diameter. The method 800 includes, at step 802, delivering an aiming beam from an aiming beam source along an aiming beam path, the aiming beam passing through a concave lens disposed between the patient and the aiming beam and configured to diverge the aiming beam around a treatment beam source such that only a portion of the aiming beam is blocked by the treatment beam source prior to passing through a convex lens disposed between the patient and the treatment beam source. At step 804, the method includes defining, via the aiming beam, a visible treatment boundary on retinal tissue of the patient, the aiming beam passing through the convex lens to be focused onto the retinal tissue to define the treatment boundary. At step 806, the method further includes delivering, via a treatment beam from the treatment beam source, a therapeutic treatment to retinal tissue of the patient's eye at a treatment spot on the retinal tissue disposed within the treatment boundary, the treatment beam being delivered along a treatment beam path extending non-coaxial relative to the aiming beam path.

Figure 9:
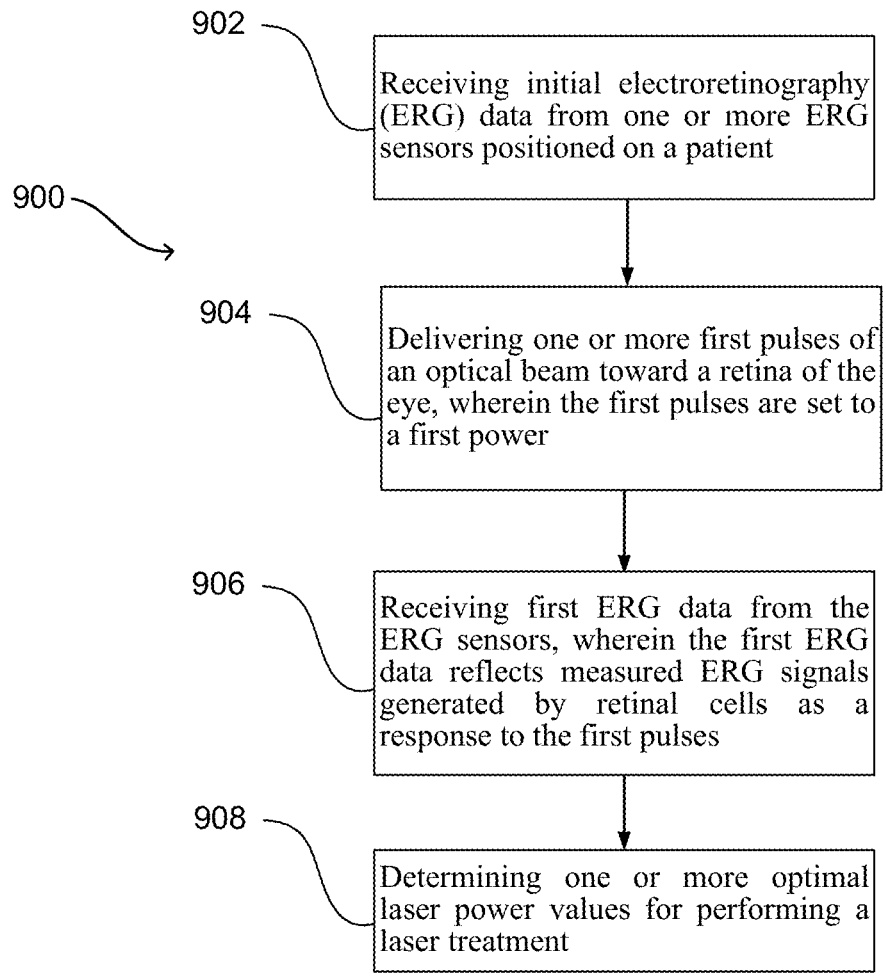
FIG. 9 is a flowchart illustrating an example method 900 providing a pre-treatment evaluation of an eye of a patient.

FIG. 9 illustrates an exemplary method 900 for providing a pre-treatment evaluation of an eye of a patient. One or more of any steps of methods described herein may be removed, re-ordered, substituted, added, or modified. At step 902, initial electroretinography (ERG) data is received from one or more ERG sensors positioned on a patient. At step 904, one or more first pulses of an optical beam are delivered toward a retina of the eye, wherein the first pulses are set to a first power. At step 906, first ERG data from the ERG sensors is received, wherein the first ERG data reflects measured ERG signals generated by retinal cells as a response to the first pulses. At step 908, one or more optimal laser power values are determined for performing a laser treatment.

In the description above, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

The use of the terms "a" and "an" and "the" and similar referents in the context of describing the invention (especially in the context of the following claims) are to be construed to cover both the singular and the plural, unless otherwise indicated herein or clearly contradicted by context. The term "or" in reference to a list of two or more items, covers all of the following interpretations of the word: any of the items in the list, all of the items in the list, and any combination of items in the list. The terms "comprising," "having," "including," and "containing" are to be construed as open-ended terms (i.e., meaning "including, but not limited to,") unless otherwise noted. The terms "connected" or "attached" are to be construed as partly or wholly contained within, coupled to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for providing a therapeutic treatment to a patient's eye, the system comprising:
    a treatment beam source configured to transmit a treatment beam along a treatment beam path, the treatment beam having an infrared wavelength and a power from 1 to 100 W;
    an aiming beam source configured to transmit an aiming beam along an aiming beam path, the aiming beam having a visible wavelength and the aiming beam path extending non-coaxially relative to the treatment beam path; and
    a processor coupled to the treatment beam source and the aiming beam source, the processor being configured to:
        direct the aiming beam onto the retinal tissue of the patient's eye at a first treatment spot and define, via the aiming beam, a treatment boundary surrounding the first treatment spot such that the first treatment spot is disposed therein;
        direct the treatment beam onto retinal tissue of the patient's eye; and
        deliver a series of pulses from the treatment beam onto the retinal tissue at the first treatment spot to treat the retinal tissue, the first treatment spot being 1 to 6 mm in diameter, wherein:
            a duration of each pulse is sufficiently short so as to avoid inducing photocoagulation of the retinal tissue that results in visible tissue damage; and
            the series of pulses directed to the first treatment spot induces photoactivation of a therapeutic healing at the first treatment spot.

2. The system of claim 1, wherein the treatment beam is configured to be directed onto the retinal tissue of the patient's eye to ensure substantially uniform tissue heating at the treatment spot without being scanned.

3. The system of claim 1, wherein the treatment beam source is a vertical-cavity surface-emitting laser (VCSEL).

4. The system of claim 1, wherein the treatment beam source is configured to be located above the patient to transmit the treatment beam in a generally downward direction toward the patient's eye such that the patient may be in a supine position during treatment.

5. The system of claim 1, wherein the first treatment spot comprises a macular region of the retinal tissue.

6. The system of claim 5, wherein the treatment beam is configured to be directed onto 80 to 100% of the macular region.

7. The system of claim 1, wherein the treatment beam heats the retinal tissue at the first treatment spot in a range of 50 to 55 degrees C.

8. The system of claim 1, wherein the treatment boundary comprises at least one of a ring or circular cross-section.

9. The system of claim 1, wherein the aiming beam has a power under 1 mW.

10. The system of claim 1, further comprising a convex lens disposed between the patient and the aiming beam source configured to focus the aiming beam onto a concentric ring on the retinal tissue surrounding the treatment beam at the first treatment spot.

11. The system of claim 10, wherein the treatment beam source is disposed between the convex lens and the aiming beam source.

12. The system of claim 11, further comprising a concave lens disposed between the aiming beam source and the treatment beam source configured to diverge the aiming beam around the treatment beam source such that only a portion of the aiming beam is blocked by the treatment beam source.

13. The system of claim 1, wherein the aiming beam is directed onto a retinal pigment epithelium of the patient's eye.

14. A method for providing a therapeutic treatment to a patient's eye, the method comprising:
    delivering an aiming beam from an aiming beam source along an aiming beam path, the aiming beam having a visible wavelength and the aiming beam path extending non-coaxially relative to a treatment beam path;
    directing the aiming beam onto the retinal tissue of the patient's eye at a treatment spot
    defining, via the aiming beam, a treatment boundary surrounding the treatment spot such that the treatment spot is disposed therein; and
    delivering, via the treatment beam from the treatment beam source, a therapeutic treatment to retinal tissue of the patient's eye, the delivered therapeutic treatment comprising the treatment spot on the retinal tissue at an intensity below that which effects coagulative damage so as to minimize damage to the retinal tissue, the treatment beam being delivered at an infrared wavelength, and along the treatment beam path and the treatment spot being 1 to 6 mm in diameter.

15. The method of claim 14, further comprising delivering a series of pulses from the treatment beam onto the retinal tissue at the treatment spot to therapeutically treat the retinal tissue, wherein a duration of each pulse is sufficiently short so as to avoid inducing photocoagulation of the retinal tissue that results in visible tissue damage, and wherein the series of pulses directed to the treatment spot induces photoactivation of a therapeutic healing at that treatment spot.

16. The method of claim 14, wherein the therapeutic treatment is delivered only to a single treatment spot on the retinal tissue.

17. The method of claim 14, further comprising heating the tissue at the treatment spot in a substantially uniform manner without scanning the treatment beam.

18. The method of claim 14, wherein the treatment beam source comprises a VCSEL array, the VCSEL array comprising a set of laser-delivery elements that are individually powered, wherein delivering the treatment beam to the treatment spot comprises:
    delivering, by the laser-delivery elements, a plurality of laser beams to a plurality of sub-spots within the treatment spot, wherein laser outputs of the laser-delivery elements are individually adjusted so as to ensure substantially uniform tissue heating at the treatment spot.

19. The method of claim 14, further comprising delivering the therapeutic treatment via a generally downward treatment beam path toward the patient's eye such that the patient may be in a supine position during treatment.

20. The method of claim 14, wherein the treatment spot comprises a macular region of the retinal tissue.

21. The method of claim 20, further comprising delivering the therapeutic treatment onto 80 to 100% of the macular region.

22. The method of claim 14, wherein directing the aiming beam onto the retinal tissue comprises directing the aiming beam through a convex lens disposed between the patient and the aiming beam source to focus the aiming beam onto a concentric ring on the retinal tissue surrounding the treatment spot.

23. The method of claim 22, wherein the treatment beam source is disposed between the convex lens and the aiming beam source.

24. The method of claim 23, wherein directing the aiming beam onto the retinal tissue comprises directing the aiming beam through a concave lens disposed between the aiming beam source and the treatment beam source to diverge the aiming beam around the treatment beam source such that only a portion of the aiming beam is blocked by the treatment beam source prior to directing the aiming beam through the convex lens.

25. The method of claim 14, wherein delivering the treatment beam onto the retinal tissue comprises delivering a series of pulses onto a retinal pigment epithelium at the treatment spot to therapeutically treat the retinal tissue, wherein a duration of each pulse is sufficiently short to allow tissue cooling between pulses which limits a temperature increase at the tissue and avoids inducing photocoagulation of the retinal tissue that results in visible tissue damage by at least one of ophthalmoscopy, fluorescein angiography or autofluorescence imaging, and wherein the series of pulses directed to the treatment spot induces intracellular, sublethal damage of retinal pigment epithelial cells which in turn improves retinal function.

26. The method of claim 14, wherein the treatment beam is delivered at an intensity below that which effects intracellular, non-lethal damage so as to minimize damage to the retinal tissue, the treatment beam being delivered at the infrared wavelength and along the treatment beam path and the treatment spot being 1 mm to 6 mm in diameter.

27. The method of claim 14, wherein the treatment beam is delivered at a power from 100 mW to 10 W or from 1 W to 100 W.

* * * * *